United States Patent [19]
Wunde et al.

[11] Patent Number: 5,173,469
[45] Date of Patent: Dec. 22, 1992

[54] SILVER CATALYST SUITABLE FOR OXIDATION OF ETHYLENE AND PROCESS FOR THE PRODUCTION OF THE CATALYST

[75] Inventors: Christian Wunde; Wilma Dibowski, both of Marl; Dietmar Kyewski, Haltern, all of Fed. Rep. of Germany

[73] Assignee: Huels Aktiengesellschaft, Marl, Fed. Rep. of Germany

[21] Appl. No.: 772,648

[22] Filed: Oct. 9, 1991

Related U.S. Application Data

[63] Continuation-in-part of Ser. No. 610,171, Nov. 9, 1990, abandoned.

[30] Foreign Application Priority Data

Nov. 9, 1989 [DE] Fed. Rep. of Germany ....... 3937247
Mar. 30, 1990 [DE] Fed. Rep. of Germany ....... 4010182

[51] Int. Cl.$^5$ ................ B01J 21/04; B01J 23/02; B01J 23/50
[52] U.S. Cl. .................. 502/340; 502/347; 502/348; 549/534
[58] Field of Search .............. 502/340, 347, 348

[56] References Cited

U.S. PATENT DOCUMENTS

| | | | |
|---|---|---|---|
| 2,424,083 | 7/1947 | Finch et al. | 502/347 |
| 3,702,259 | 11/1972 | Nielsen | 502/348 X |
| 4,248,740 | 2/1981 | Mitsuhata et al. | 502/348 |
| 4,305,844 | 12/1981 | Vangermain et al. | 252/443 |
| 4,690,913 | 9/1987 | Nojiri et al. | 502/347 X |
| 4,760,042 | 7/1988 | Armstrong | 502/243 |
| 4,769,358 | 9/1988 | Kishimoto et al. | 502/347 X |
| 4,841,080 | 6/1989 | Armstrong | 549/536 |
| 5,063,195 | 11/1991 | Jin et al. | 502/341 |

FOREIGN PATENT DOCUMENTS

| | | |
|---|---|---|
| 0017725 | 2/1980 | European Pat. Off. . |
| 0327356 | 8/1989 | European Pat. Off. . |
| 3334347 | 9/1983 | Fed. Rep. of Germany . |
| 2117183 | 7/1972 | France . |
| 2117263 | 10/1983 | United Kingdom . |

*Primary Examiner*—W. J. Shine
*Attorney, Agent, or Firm*—Millen, White, Zelano and Branigan

[57] ABSTRACT

A silver catalyst suitable for the oxidation of ethylene is provided in which the silver within a support particle, e.g., alumina, is non-uniformly distributed so that the silver concentration is clearly greater on the geometric surface and in the surface layer just beneath less than 0.5 mm thick than in the interior of the particles. The concentration of silver in the layer is two to a thousand times the concentration in the interior of the catalyst.

25 Claims, No Drawings

SILVER CATALYST SUITABLE FOR OXIDATION OF ETHYLENE AND PROCESS FOR THE PRODUCTION OF THE CATALYST

CROSS-REFERENCE TO RELATED APPLICATION

This is a continuation-in-part application of application Ser. No. 07/610,171, filed Nov. 9, 1990, now abandoned.

BACKGROUND OF THE INVENTION

The invention relates to a silver catalyst suitable for the oxidation of ethylene with oxygen and a process for the production of said catalyst.

As is known, silver catalysts are used for the production of ethylene oxide by the controlled incomplete oxidation of ethylene with molecular oxygen. Numerous modifications of the silver catalyst have already been proposed. It is known from DE-20 17 733, DE-29 14 640, as well as DE-33 34 347, to precipitate metallic silver from silver-containing suspensions or mixtures of suspensions and solutions on slightly porous catalyst supports. In these catalysts, the silver is present according to experience in a largely continuous layer with variable thickness, which consists of relatively large silver particles and covers the surface of the support as well as the walls of the channels and holes in the support. Such a layer can easily be mechanically damaged; as a result silver dust occurs in the reaction pipe, and the pressure difference between the ends of the reaction pipe increases during the operation. As a result, the gas throughput and the performance of the reactor decrease. In such catalysts, produced according to the "suspension process," the activity and selectivity decrease particularly fast.

It is also known from DE-21 59 346 and EP-0 161 930 to produce silver catalysts according to the impregnation process. In this case, a highly porous catalyst support is immersed in a solution of one or more silver compounds. Such impregnated catalysts do exhibit favorable aging characteristics, but generally at the beginning of their use period, they have a lower activity and selectivity than suspension catalysts. To counteract the decrease in selectivity, the selectivity of impregnated catalysts can be improved according to DE-23 00 512, DE-27 34 912, EP-0 266 015, and EP-0 229 465 by alkali metal and other promoters being additionally precipitated on the support. But according to experience, a favorable doping of promoters for improvement of selectivity results in a loss of activity. By a choice of the type and amount of suitable promoters alone, a highly selective and at the same time highly active catalyst cannot be produced.

According to DE-33 21 895 impregnated catalysts are doped with alkali and alkaline-earth promoters in comparatively high concentration and then heated to temperatures of 450° C. to 800° C. to increase the activity, but according to experience, even with these catalysts, activity and selectivity are still in need of improvement.

SUMMARY OF THE INVENTION

Thus, an object of the invention is to provide an improved silver catalyst which, on the basis of the same silver content, has an improved activity and selectivity in comparison with the usual silver catalysts.

Another object is to provide a process for the preparation of such catalysts.

Still another object is to provide a process of using these catalysts to produce ethylene oxide.

Upon further study of the specification and appended claims, further objects and advantages of this invention will become apparent to those skilled in the art.

These and other objects are achieved according to the invention by providing a silver catalyst with the following features:

(a) as support, lumpy, highly porous heat-resistant material such as, e.g., α-aluminum oxide;

(b) 0.1 to 25% by weight of metallic silver, relative to the weight of the finished catalyst, which is present in finely dispersed form on the inside and outside support surface;

(c) inside a support particle, a nonuniform concentration of the silver, which on the geometric surface and in a layer immediately under the geometric surface of support particle is clearly greater than in the interior of the support particle. By "geometric" is meant the surfaces on the outside of the particle. Thus, for example, both a porous and non-porous sphere of the same diameter have the same geometric surface.

The layer lying under the geometric surface of the support particle having a clearly greater concentration of silver than the interior of the particle has a thickness of less than 0.5 mm, preferably less than 0.3 mm, measured perpendicularly from the geometric surface. The concentration of the silver in the layer is four to a thousand times the concentration of the silver inside the support particle. It is also contemplated that the concentration be at least 5, 6, 7, 8, 9 or 10 times the concentration inside the support particle. The preferred thickness of said layer just underneath the geometric surface is about 0.01 mm and, for example, the concentration of the silver in the layer is ten to a thousand times the concentration of the silver inside the support particle.

After the thermal forming of the catalyst, most of the silver particles have a diameter of 0.01 to 1 micron.

Besides silver, the catalyst can contain sodium, potassium, rubidium, cesium and/or barium compounds, preferably in an amount of 0.0005 to 0.03 gram equivalent per kilogram of catalyst.

The highly porous heat-resistant support has a BET surface of 0.05–2 m$^2$/g and preferably consists essentially of α-aluminum oxide having a purity of more than 80% by weight.

The catalyst according to the invention is produced by a process having the following features:

(1) selection of such moderately soluble silver compounds and formulations which at 50° C. produce a saturated solution with less than 400 g of silver, preferably less than 330 g of silver, per liter of solution;

(2) adjustment of the silver concentration of the impregnating solution to a value of 10–90% of the saturation concentration at the impregnating temperature;

(3) adjustment of the temperature during impregnation of the support to a value, at which the silver compound remains in solution;

(4) predrying of the impregnated support at a temperature of 40° C. to 120° C., preferably 60° C. to 90° C.; and (5) thermal forming of the support in a gas stream.

As solvent for the silver-containing solution, there is employed water or an optionally aqueous organic liquid, such as, e.g., ethanol, or a mixture of optionally aqueous organic liquids.

Instead of selecting a silver compound, a colloidal silver solution can be used, and the silver colloid can be present either unprotected or protected, e.g., by another colloid. Such colloidal silver solutions can, if desired, be purchased commercially.

The catalyst support is impregnated with the silver-containing solution and is predried in a moving or fixed bed. The vessel, which contains the impregnated support, can be repeatedly evacuated during the impregnation and predrying. During predrying the pressure is between 20 kPa (200 mbars) and 50 kPa (500 mbars). The predrying takes at least 30 minutes, preferably at least 60 minutes. The impregnation and predrying vessel can be repeatedly aerated and evacuated, namely at intervals of 1 to 30 minutes, preferably 5 to 15 minutes, especially 3 to 15 minutes. After the predrying, the support is further dried in a gas stream at 50° C. to 150° C. and then, as usual, thermally formed into a thin moving layer, preferably during 5 to 240 minutes at a temperature of the forming gas of 100° C. to 250° C. The forming gas is preferably composed predominantly of nitrogen and contains 12% oxygen at most. During forming, support particles lie in a moving layer with a layer thickness, which corresponds to one-fold to five-fold the smallest dimension of a support particle.

Suitable highly porous supports for the catalysts according to the invention are commercial alpha-aluminum oxides having the aforementioned BET surface of 0.05-2 $m^2/g$ and a particle diameter of 5 to 10 mm. The support particles can be annular, spherical or shaped some other way.

From the diameter of the support particles (5 to 10 mm) and the thickness of the layer under the geometric surface of the support particle having a clearly greater concentration of silver than the interior of the particle (less than 0.5 mm, preferably less than 0.3 mm and most preferably about 0.01 mm) the ratio of the volume of the silver-containing layer immediately underneath the geometric surface to the total volume of the support particle can be derived if the shape of the support particle is determined. For example, for a spherical support particle with 5 mm diameter and a thickness of the silver-containing layer of less than 0.5 mm, preferably less than 0.3 mm and most preferably about 0.01 mm, the ratio of the volume of the silver-containing layer to the total volume of the support particle is less than 48.9%, preferably less than 31.9% and most preferably about 1.2%.

The impregnating process can be one stage or multistage. The promoter compounds can be precipitated at the same time with the silver compounds or separately.

As it was surprisingly shown, a silver catalyst, in which the silver is concentrated in a thin layer on and under the geometric surface of the support particles, has favorable properties. Such a catalyst is obtained, if, during impregnation of the support particles with the silver-containing solution and during predrying of the impregnated support particles, such process conditions are maintained, which favor the precipitation of the silver compounds or precipitation of the metallic silver on the geometric surface and the near-surface layer of the highly porous support. In this case, the solubility of the silver compound in the selected solvent, the viscosity of the solution or the suspension and optionally the size of the colloidal particles and their electrical interfacial properties at the temperature present during the impregnation and during predrying are to be taken into account for an optimum process.

Moreover, during predrying and during forming, the following parameters may, either individually or in combination, have an effect:

(i) the temperatures (the starting and end temperatures can be different) in view of the respective silver compound used;

(ii) aeration of the partially evacuated impregnation and drying vessel in optimized periods and intervals in view of the silver compounds, the solvent, the container size and batch size as well as the heating of the container;

(iii) the final pressure during predrying under partial vacuum;

(iv) the control of the pressure, which determines the period of the drying process under reduced pressure;

(v) the gas composition, gas temperature and flow rate in the drying and forming in the gas stream;

(vi) the thickness of the catalyst layer during drying and forming; and (vii) the respective retention times of the support particles during the different phases of these treatment processes.

Consequently, for any given system, experimentation will be required to obtain the optimum results.

The intensified precipitation of silver compounds in the near-surface layer of the highly porous support particles is caused, e.g., by chromatography effects. It is further influenced by initiators, e.g., barium peroxide, which favor the formation of seed crystals.

The distribution of the silver within the support particles of the finished catalyst can be determined by a scanning electron microscope with a device for energy-dispersive x-ray analysis (EDX).

The catalyst according to the invention has the following advantages:

The activity of the catalyst is clearly higher in comparison with the activity of generic catalysts, whose silver content is as high or somewhat higher, with unchanged or somewhat increased selectivity. The catalyst of the invention can also be used at a lower operating temperature.

The catalyst ages more slowly than a comparable catalyst according to the prior art. As a result, its shelf life is greater and the amount of silver necessary for the production of a certain amount of ethylene oxide is less.

By the non-uniform distribution of the silver within the support particle and the concentration in a thin layer on and under the geometric surface of the support, the mass transfer and heat transfer during the normal gas phase reaction are favored, and the reaction can be performed more suitably. In catalysts according to the prior art, in which the silver within the highly porous support is distributed approximately uniformly, the silver particles located in deeper layers of the catalyst generally make only a relatively small contribution to the partial oxidation of ethylene to ethylene oxide, and the reaction heat released within the support particles is generally dissipated more slowly by gas transport than the reaction heat, which is released on the surface of the catalyst support.

Within the highly porous support particles of the catalyst according to the invention even less ethylene oxide is produced than in a catalyst according to the prior art. As a result, the percentage of ethylene oxide, which is isomerized to acetaldehyde or further oxidized to carbon dioxide and water is lower and thus the selectivity is somewhat greater.

The amount of catalyst dust produced in the reaction pipes during the operation is smaller than in the conventional catalysts produced according to the suspension process.

Because of the lower operating temperature, the oxygen content can be increased in the circulating gas, which has a favorable effect on the selectivity and aging properties of the catalyst.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, if any, cited herein, and of corresponding Applications P 39 37 247.2 and P 40 10 182.7, filed in the Federal Republic of Germany on Nov. 9, 1989, and Mar. 30, 1990, respectively, are hereby incorporated by reference.

EXAMPLES

For the production of the catalysts according to the invention, and for comparison produced according to the prior art, different commercial supports made from alpha-aluminum oxide with different chemical composition and different physical properties as well as different particle size and shape are used; these supports are listed in Table 1.

TABLE 1

|  | Support A | Support B | Support C | Support D | |
|---|---|---|---|---|---|
| Aluminum oxide content | 95 | 95 | 86 | 97 | wt. % |
| Particle diameter | 6.2 | 8.5 | 8.5 | 7.2 | mm |
| Particle shape | annular | annular | spherical | annular | |
| Hole diameter | 2.6 | 3.2 | — | 3.5 | mm |
| Particle length | 6.0 | 7.9 | — | 6.4 | mm |
| Specific surface | 0.35 | 0.35 | 0.29 | 0.43 | m$^2$/g |
| Pore volume | 0.39 | 0.43 | 0.35 | 0.41 | cm$^3$/g |
| Bulk density | 758 | 695 | 825 | 747 | g/l |
| Water absorption | 37 | 39 | 41 | 44 | wt. % |
| Average pore diameter | 5.2 | 8.6 | — | 3 | micron |

The annular shape is like a hollow cylinder.

If in impregnating a support with solutions which contain the silver in a low concentration (e.g., colloidal solutions), a single immersion is not sufficient, a multiple immersion is necessary.

EXAMPLE 1

413 g of silver nitrate is dissolved in 2 liters of water and reacted to silver oxide with 25% aqueous sodium hydroxide solution. The silver oxide is separated from the sodium hydroxide solution with a suction filter, washed alkali-free with water, transferred into a vessel and suspended with 750 ml of water. With 315 g of lactic acid preheated to 70° C., a silver lactate solution is produced, which is mixed with 0.55 g of barium peroxide and diluted with water to 1500 ml.

With this silver lactate solution, 3.3 liters of support A (see Table 1) is impregnated in a rotary evaporator. The remainder of the impregnating solution not absorbed by the support remains in the flask of the rotary evaporator. The bath temperature of the rotary evaporator is adjusted to 70° C., and the solvent is removed at partial vacuum. Every 7 minutes, the flask is aerated and kept under normal pressure for 5 minutes. After 3 to 4 hours, a pressure of 20 kPa (200 mbars) is reached in the flask.

The impregnated and predried support is then dried on an electrically heated screen belt machine, first at an adjusted temperature of 80° C. and then at 120° C. The retention time is about 55 minutes on the screen belt machine which has a length of 3.2 m and at a belt speed of about 6 cm/minute. The support particles lie on the belt in a layer, having a thickness corresponding approximately to twice the particle diameter.

Then the support particles are formed on the screen belt machine for 55 minutes at 180° C. in a nitrogen-air mixture, which contains about 7% oxygen; thus the silver compound is decomposed.

Now, as described above, a second silver lactate solution is produced, with which additionally 1.41 g of cesium nitrate is mixed. The support particles already impregnated and formed once are again impregnated with this solution and again predried but now are formed once more for 55 minutes at 240° C. on the screen belt machine.

The silver is clearly concentrated on the outer surface of the support particles of the finished catalyst and in the near-surface layer about 0.2 mm thick, in comparison with the inside of the support particles.

EXAMPLE 2

3.3 liters of support B (see Table 1) is impregnated, predried, and formed analogously to Example 1.

The silver solution for the second impregnation is mixed with 1.17 g of cesium nitrate and 0.55 g of barium peroxide. With it the support is impregnated a second time and predried and formed analogously to Example 1.

The silver is clearly concentrated on the outer surface of the support particles of the finished catalyst and in the near-surface layer about 0.2 mm thick, in comparison with the inside of the support particles.

EXAMPLE 3

3.3 liters of support C (see Table 1) analogously to Example 1 is impregnated, predried, and formed.

The silver solution for the second impregnation is mixed with 0.99 g of cesium nitrate, 3.0 g of sodium nitrate and 0.55 g of barium peroxide. With it, the support is impregnated a second time and predried and formed analogously to Example 1.

The silver is clearly concentrated on the outer surface of the support particles of the finished catalyst and in the near-surface layer about 0.2 mm thick, in comparison with the core of the support particles.

EXAMPLE 4

A silver lactate solution with corresponding volume is produced from 826 g of silver nitrate, 630 g of lactic acid and 1.1 g of barium peroxide analogously to Example 1. This solution is diluted with water to 5.5 liters and heated to 70° C.

6.6 liters of support D (see Table 1) is poured into a cylindrical vessel holding about 8 liters with jacket heating; the jacket heating is adjusted to 70° C. The support is doused with hot silver lactate solution at 70° C., and for about 5 minutes a partial vacuum is created. After the aeration, the part of the solution not absorbed by the support is discharged. The support is predried in this vessel for about one hour at 70° C. and under partial vacuum. The partial vacuum during predrying is disrupted twice for about 7 minutes.

The support is doused twice more with the remaining part of the 70° C. solution and then predried each time in the described way.

The support, doused three times and predried, is dried in a glass vessel for 12 hours at 80° C. by a nitrogen stream and then, analogously to Example 1, formed on the screen belt machine for 55 minutes at 180° C.

Further, a solution is produced from 826 g of silver nitrate, 630 g of lactic acid as well as 2.3 g of cesium nitrate and 1.1 g of barium peroxide, and diluted with water to 5.5 liters.

The already formed support is doused once more with this solution, predried and again formed on the screen belt machine for 55 minutes at 240° C.

The silver is clearly concentrated on the outer surface of the support particles of the finished catalyst and in the near-surface layer about 0.3 mm thick, in comparison with the inside of the support particles.

EXAMPLE 5

Analogously to Example 1, a silver lactate solution is produced from 45 g of silver nitrate and 34.3 g of lactic acid, and diluted with water to 125 ml. 25 g of ethanol, 0.10 g of cesium nitrate and 0.11 g of barium peroxide are added to this solution and stirred intensively.

Analogously to Example 1, 0.33 liters of support A (see Table 1) is impregnated with this solution, predried and formed on the screen belt machine for 55 minutes at 180° C.

The silver is clearly concentrated on the outer surface of the support particles of the finished catalyst and in the near-surface layer about 0.2 mm thick, in comparison with the inside of the support particles.

EXAMPLE 6

Analogously to Example 1, a silver lactate solution is produced from 10.3 g of silver nitrate and 7.9 g of lactic acid, and diluted with water to 120 ml. 0.11 g of barium peroxide is added to this solution and intensively stirred.

Analogously to Example 1, 0.33 liters of support A (see Table 1) is impregnated with such a solution, predried and formed, namely four times.

With these support particles of the finished catalyst, provided with four silver coats, the silver is especially clearly concentrated on the outer surface and in the near-surface layer about 0.3 mm thick, in comparison with the inside of the support particles.

EXAMPLE 7

A silver lactate solution is produced from 20.6 g of silver nitrate and 16.5 g of lactic acid analogously to Example 1 and diluted with water to 50 ml.

Another 20.6 g of silver nitrate is converted into a silver oxide suspension analogously to Example 1 and converted into a silver malonate suspension by addition of a solution of 5.5 g of malonic acid in 15 g of water.

The two silver-containing liquids are combined; a mixture of 18.3 g of isopropylamine and 18.3 g of tert-butylamine is slowly instilled with stirring and cooling. This solution is diluted with water to 150 ml and mixed with 0.11 g of barium peroxide.

Analogously to Example 1, 0.33 liters of support A (see Table 1) is impregnated with this solution, predried and formed.

The silver is clearly concentrated on the outer surface of the support particles of the finished catalyst and in the near-surface layer about 0.2 mm thick, in comparison with the inside of the support particles.

EXAMPLE 8

Analogously to Example 1, a silver oxide suspension is produced from 45 g of silver nitrate and then an aqueous silver oxalate suspension is produced with 17.5 g of oxalic acid dihydrate. The silver oxalate suspension is converted with a mixture of 20 g of isopropylamine and 20 g of tert-butylamine, with stirring and cooling, into a clear solution, and 0.11 g of barium peroxide is added with stirring. This solution is diluted with water to 150 ml.

Analogously to Example 1, 0.33 liters of support A (see Table 1) is impregnated with this solution, predried and formed.

The silver is very clearly concentrated on the outer surface of the support particles of the finished catalyst and in the near-surface layer about 0.1 mm thick, in comparison with the inside of the support particles.

EXAMPLE 9

A silver oxide suspension is produced from 45 g of silver nitrate analogously to Example 1. The silver oxide is reacted with 200 g of dry ice to silver carbonate, the latter is reacted with a mixture of 26 g of isopropylamine and 26 g of tert-butylamine with stirring and cooling to the corresponding silver amine complexes, diluted with water to 150 ml and intimately mixed with 0.11 g of barium peroxide.

0.33 liters of support A (see Table 1) is impregnated with the solution, preheated to 70° C., predried and, analogously to Example 1, formed at 180° C.

The silver is very clearly concentrated on the outer surface of the support particles of the finished catalyst and in the near-surface layer about 0.1 mm thick, in comparison with the inside of the support particles.

EXAMPLE 10

37 g of support A (see Table 1) in a rotary evaporator under partial vacuum and at room temperature is impregnated with 100 ml of a colloidal silver solution (producer Degussa; 0.8% silver in aqueous solution with protective colloid (polyoxy-carboxylic acid); the flask is aerated twice within 10 minutes and kept at normal pressure for 1 minute. The residual solution not absorbed by the catalyst support is decanted. The solvent is removed under partial vacuum. The bath temperature is raised from room temperature to 95° C. within 10 minutes. Then the flask is aerated every 7 minutes and kept at normal pressure for 5 minutes. After about 35 minutes a pressure of 20 kPa (200 mbars) is reached in the flask.

The impregnated and predried support is then dried on an electrically heated screen belt machine first at an adjusted temperature of 105° C. in a nitrogen-air mixture with about 7% oxygen. The screen belt machine has a length of 3.2 m; at a belt speed of about 6 cm/minute, the retention time is about 55 minutes. The support particles lie on the belt in a layer having a thickness corresponding approximately to twice the particle diameter.

Then the particles are formed on the screen belt machine for 55 minutes at 200° C. in a nitrogen-air mixture, which contains about 7% oxygen.

The particles, as described above, are impregnated twice more, predried in the rotary evaporator and dried and formed on the screen belt machine as described above.

The silver is very clearly concentrated on the outer surface of the support particles of the finished catalyst and in the near-surface layer about 0.2 mm thick, in comparison with the inside of the support particles. The central areas of the support particles are almost free of silver. The diameter of the silver particles is predominantly under 0.1 micron.

EXAMPLE 11

37 g of support A (see Table 1) in a rotary evaporator is impregnated with 20 ml of a colloidal silver solution (see Example 10). The residue of impregnating solution, not absorbed by the support, remains in the flask. During the first 10 minutes the bath of the rotary evaporator is at room temperature. Then the bath temperature is raised to 95° C. within about 10 minutes. The solvent is removed under partial vacuum. The flask is aerated every 7 minutes and kept at normal pressure for 5 minutes. After about 50 minutes a pressure of 20 kPa (200 mbars) is reached in the flask.

The impregnated and predried support is dried and formed, as described in Example 10, at 105° C. on a screen belt machine electrically heated and then at 200° C. in a gas stream of a nitrogen-air mixture, which contains about 7% oxygen.

Now the catalyst particles are impregnated once more, predried in the rotary evaporator, and dried and formed on the screen belt machine, as described above.

The silver is very clearly concentrated on the outer surface of the support particles of the finished catalyst and in the near-surface layer about 0.2 mm thick, in comparison with the inside of the support particles. The central areas of the support particles contain only few solitary silver particles. The diameter of the silver particles is predominantly under 0.1 micron.

EXAMPLE 12

37 g of support B (see Table 1), in a rotary evaporator as described in Example 11, is impregnated with 20 ml of a colloidal silver solution (see Example 10), and predried, and dried and formed on a screen belt machine analogously to Examples 10 and 11. Another impregnating with predrying, drying and forming follows according to the same method.

The silver is very clearly concentrated on the outer surface of the support particles of the finished catalyst and in the near-surface layer about 0.2 mm thick, in comparison with the inside of the support particles. The central areas of the support particles contain only few solitary silver particles. The diameter of the silver particles is predominantly under 0.1 micron.

EXAMPLE 13

400 ml of a colloidal silver solution (see Example 10) is concentrated by evaporation in the rotary evaporator under reduced pressure to 100 ml.

37 g of support B (see Table 1), corresponding to the process indicated in Example 11, is impregnated twice with 20 ml each of the colloidal silver solution, concentrated by evaporation, predried, dried and formed, as described above.

The silver is very clearly concentrated on the outer surface of the support particles of the finished catalyst and in the near-surface layer about 0.2 mm thick, in comparison with the inside of the support particles. The diameter of the silver particles is predominantly under 0.1 micron.

Because of the tendency of some amine-containing silver formulations possibly to decompose very violently in the predried state, amine-free formulations are preferable.

The catalysts produced according to the invention and for purposes of comparison according to the prior art are tested in a device, which comprises a reaction pipe 6 m long and 26 mm in diameter made of stainless steel. The reaction pipe is surrounded by a jacket, which contains water or steam for removal of the reaction heat. The reaction pipe is filled with 2.7 liters each of finished catalyst.

A gas mixture, consisting of:
30% by vol. of $C_2H_4$,
50% by vol. of $CH_4$,
6.8% by vol. of $O_2$,
4.0% by vol. of $CO_2$,
0.3% by vol. of $C_2H_6$,
residue Ar and $N_2$
is conducted over the catalyst with a throughput of 20 $Nm^3/h$. The pressure in the reactor is 1.9 MPa (19 bars). A chlorine-containing moderator is added to the gas mixture so that the total gas chlorine content in the reaction gas is about 8 mg of chlorine/$Nm^3$.

The finished catalysts according to the invention described in the examples, in which the silver is clearly concentrated on the geometric surface and near-surface layer, show in direct comparison with corresponding known finished catalysts which were produced from the same respective support and with the same respective silver content and the same dopants, but exhibit over the entire cross section of the support particles a uniform silver distribution, activity improvements, which correspond to a lowering of the reaction temperature of 5 to 10 degrees, and selectivity improvements of 0.3 to 1.0% at the same production rate of ethylene oxide.

The thickness of the layer containing a concentration of silver substantially higher than the interior of the support particles is substantially independent of the size of the support particle.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A silver catalyst suitable for the oxidation of ethylene to ethylene oxide, said catalyst comprising a content of 0.1 to 25% by weight of silver, relative to the weight of finished catalyst, on porous heat-resistant support particles, produced by impregnation of the support particles with a silver-containing solution in one or more stages and precipitation of metallic silver on the support particles, said support particles containing a non-uniform concentration of the metallic silver such that on outer geometric surfaces and in layers of said support particles immediately underneath the geometric surface are containing concentrations of silver four to a thousand times greater than in the interior of said support particles.

2. A catalyst according to claim 1, wherein the silver concentration in said layers immediately under the geometric surface has a concentration of silver ten to a thousand times greater than the concentration in the interior of the support particles.

3. A silver catalyst according to claim 1, wherein said underneath surface layer of the support particles has a substantially greater concentration of silver which is less than 0.5 mm thick.

4. A silver catalyst according to claim 3, wherein said thickness is less than 0.3 mm.

5. A silver catalyst according to claim 1, wherein said metallic silver is present as particles having mostly a diameter of 0.01 to 1 micron.

6. A silver catalyst according to claim 2, wherein said metallic silver is present as particles having mostly a diameter of 0.01 to 1 micron.

7. A silver catalyst according to claim 3, wherein said metallic silver is present as particles having mostly a diameter of 0.01 to 1 micron.

8. A silver catalyst according to claim 1, further comprising promoters selected from the group consisting of sodium, potassium, rubidium, cesium, barium, and mixtures thereof compounds in a concentration of 0.0005 to 0.03 gram equivalent per kilogram of catalyst.

9. A silver catalyst according to claim 1, said support having a BET surface of 0.05-2 m²/g.

10. A silver catalyst according to claim 9, wherein the support comprises α-aluminum oxide in a purity of more than 80% by weight.

11. A process for the production of a silver catalyst according to claim 1, in which a highly porous, heat-resistant support is impregnated in a vessel with a silver-containing impregnating solution, and the impregnated support is predried and thermally formed, comprising:
employing in said impregnating solution colloidal silver or one or more silver compounds having a solubility which provides at 50° C. a saturated solution with less than 400 g of silver per liter, said impregnating solution having a concentration of 10-90% of the saturation concentration at impregnating temperatures;
predrying the resultant impregnated support at a temperature of 40° C. to 120° C.; and
thermally forming the support in a gas stream.

12. A process according to claim 11, wherein the concentration of silver in the solution is less than 330 g and the predrying is conducted at 60°-90° C.

13. A process according to claim 12, wherein said silver solution comprises water, at least one organic liquid, or mixtures thereof as solvent for the silver compounds.

14. A process according to claim 13, said predrying of the support being conducted by passing a gas stream through or over the impregnated support.

15. A process according to claim 13, wherein said predrying of the impregnated support is conducted at a reduced pressure between 20 kPa (200 mbars) and 50 kPa (500 mbars) absolute, for at least 30 minutes.

16. A process according to claim 13, wherein said predrying of the impregnated support is conducted at a reduced pressure between 20 kPa (200 mbars) and 50 kPa (500 mbars) absolute, for at least 60 minutes.

17. A process according to claim 13, comprising aeration and evacuation of the impregnating and drying vessel at intervals of 1-30 minutes.

18. A process according to claim 13, comprising aeration and evacuation of the impregnating and drying vessel at intervals of 5-15 minutes.

19. A process according to claim 13, further comprising precipitating promoter compounds on the support particles at the same time with the silver compounds or separately from the precipitation of the silver compounds.

20. A process for the production of a silver catalyst according to claim 1, in which a highly porous, heat-resistant support is impregnated in a vessel with a silver-containing impregnating solution, and the impregnated support is predried and thermally formed, comprising:
employing as said impregnating solution a colloidal silver solution,
predrying the resultant impregnated support at a temperature of 40°-120° C., and
thermally forming the support in a gas stream.

21. A process according to claim 20, wherein the silver colloid is protected by another colloid.

22. A process for the production of a silver catalyst according to claim 1, in which a highly porous, heat-resistant support is impregnated in a vessel with a silver-containing impregnating solution, and the impregnated support is predried and thermally formed, comprising:
employing in said impregnating solution an initiation for the formation of seed crystals and one or more silver compounds having a solubility which provides at 50° C. a saturated solution with less than 400 g of silver per liter, said impregnating solution having a concentration of 10-90% of the saturation concentration at impregnating temperatures;
predrying the resultant impregnated support at a temperature of 40°-120° C.; and
thermally forming the support in a gas stream.

23. A process according to claim 22 wherein said initiator is barium peroxide.

24. A process for the production of a silver catalyst according to claim 1, in which a highly porous, heat-resistant support is impregnated in a vessel with a silver-containing impregnating solution, and the impregnated solution is predried and thermally formed, comprising:
employing in said impregnating solution colloidal silver or one or more silver compounds having a solubility which provides at 50° C. a saturated solution with less than 400 g of silver per liter, said impregnating solution having a concentration of 10-90% of the saturation concentration at impregnating temperatures;
predrying the resultant impregnated support at a temperature of 40°-120° C.; and
thermally forming resultant predried support particles into a moving layer having a layer thickness corresponding to one-fold to five-fold the smallest dimension of a support particle, by a gas stream comprised mainly of nitrogen with up to 12% by weight of oxygen, for 5-240 minutes at a temperature of 100-250° C.

25. A silver catalyst according to claim 1, produced by a process in which a highly porous, heat-resistant support is impregnated in a vessel with a silver-containing impregnating solution, and the impregnated support is predried and thermally formed, comprising:

employing in said impregnating solution colloidal silver or one or more silver compounds having a solubility which provides at 50° C. a saturated solution with less than 400 g of silver per liter, said impregnating solution having a concentration of 10-90% of the saturation concentration at impregnating temperatures;

predrying the resultant impregnated support at a temperature of 40°-120° C.; and thermally forming the support in a gas stream.

* * * * *